United States Patent [19]
Bacon et al.

[11] Patent Number: 5,348,727
[45] Date of Patent: Sep. 20, 1994

[54] COMPOSITIONS OF IODOPHENOXY ALKYLENE ETHERS FOR VISUALIZATION OF THE GASTROINTESTINAL TRACT

[75] Inventors: Edward R. Bacon, Audubon, Pa.; Carl R. Illig, Phoenixville, Pa.; Thomas J. Caulfield, Audubon, Pa.; Brent D. Douty, Coatesville, Pa.; Kurt A. Josef, Wayen, Pa.

[73] Assignee: Sterling Winthrop Inc., Malvern, Pa.

[21] Appl. No.: 29,485

[22] Filed: Mar. 11, 1993

[51] Int. Cl.$^5$ .................. A61B 5/055; C07C 41/00; A61K 31/075
[52] U.S. Cl. .................. 424/5; 514/520; 514/522; 514/570; 514/716; 514/718; 514/720; 558/414; 558/423; 562/470; 568/649
[58] Field of Search .................. 424/5; 568/649; 514/716, 718, 720, 520, 522, 570; 558/414, 423; 562/470

[56] References Cited

U.S. PATENT DOCUMENTS

| | | | |
|---|---|---|---|
| 2,348,231 | 5/1944 | Strain et al. | 260/476 |
| 2,416,263 | 2/1947 | MacMullen | 260/613 |
| 2,622,100 | 12/1952 | Newbery et al. | 260/612 |
| 2,963,474 | 12/1960 | Wiegert et al. | 260/211 |
| 3,043,881 | 7/1962 | Wismer | 568/649 |
| 3,056,843 | 10/1962 | Wismer | 568/649 |
| 3,131,166 | 4/1964 | Harris et al. | 260/47 |
| 3,360,436 | 12/1967 | Felder et al. | 167/95 |
| 3,361,700 | 1/1968 | Archer et al. | 260/31.4 |
| 3,363,003 | 1/1968 | Bolhofer | 568/649 |
| 3,366,625 | 1/1968 | Hebky et al. | 260/211 |
| 3,553,259 | 1/1971 | Felder et al. | 260/519 |
| 3,574,718 | 4/1971 | Bjork et al. | 260/501.11 |
| 3,795,698 | 3/1974 | Soulal et al. | 260/471 R |
| 3,825,591 | 7/1974 | Felder et al. | 260/519 |
| 3,883,578 | 5/1975 | Gries | 260/471 R |
| 4,005,150 | 1/1977 | Sorm et al. | 260/613 D |
| 4,333,952 | 6/1982 | McDonald | 424/330 |
| 4,568,497 | 2/1986 | Mendoza et al. | 260/465 F |
| 4,997,989 | 3/1991 | Smuda et al. | 568/649 |

FOREIGN PATENT DOCUMENTS 1259565  9/1989  Canada .
1481943  5/1967  France .

*Primary Examiner*—Gary E. Hollinden
*Attorney, Agent, or Firm*—Arthur Rosenstein; Imre (Jim) Balogh

[57] ABSTRACT

A compound of the formula:

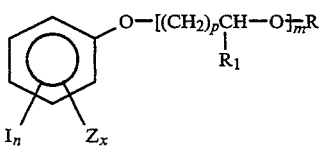

wherein
Z=H, halo, $C_1$–$C_{20}$ alkyl, cycloalkyl, lower alkoxy, alkoxycarbonyl, cyano, wherein thealkyl and cycloalkyl groups can be substituted with halogen or halo-lower-alkyl groups;
R=$C_1$–$C_{25}$ alkyl, cycloalkyl,

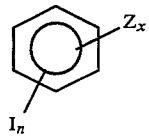

or halo-lower-alkyl; each of which may be optionally substituted with halo, fluoro-lower-alkyl, aryl, lower-alkoxy, hydroxy, carboxy, lower-alkoxy carbonyl or lower-alkoxy-carbonyloxy, $(CR_1R_2)_p$-$(CR_3{=}CR_4)_m$Q, or $(CR_1R_2)_p$—C≡C-Q;
$R_1$, $R_2$, $R_3$ and $R_4$ are independently H, or lower-alkyl, optionally substituted with halo;
x is 1–4;
n is [1–5]1–4;
m is 1–15;
p is 1–20; and
Q is H, lower-alkyl, lower-alkenyl, lower-alkynyl, lower-alkylene, aryl, these compounds are useful as X-ray contrast agents or aryl-lower alkyl.

6 Claims, No Drawings

COMPOSITIONS OF IODOPHENOXY ALKYLENE ETHERS FOR VISUALIZATION OF THE GASTROINTESTINAL TRACT

BACKGROUND OF THE INVENTION

Field of the Invention

This invention relates to aqueous compositions containing an iodophenoxy alkylene ether as the contrast agent and methods for their use in diagnostic radiology of the gastrointestinal tract.

Reported Developments

Roentgenographic examination utilizing X-rays and computed tomography (hereinafter CT) scans of fractures and other conditions associated with the skeletal system is routinely practiced without the use of contrast agents. X-ray visualization of organs containing soft tissue, such as the gastrointestinal (hereinafter GI) tract, requires the use of contrast agents which attenuate X-ray radiation. D. P. Swanson, et al in "Pharmaceuticals In Medical Imaging", 1990, MacMillan Publishing Company, provides an excellent background in medical imaging utilizing contrast agents and compositions therewith.

Roentgenographic examination of the GI tract is indicated conditions of digestive disorders, changes in bowel habit, abdominal pain, GI bleeding and the like. Prior to radiological examination, administration of a radiopaque contrast medium is necessary to permit adequate delineation of the respective lumen or mucosal surface from surrounding soft tissues. Accordingly, a contrast medium is administered orally to visualize the mouth, pharynx, esophagus, stomach, duodenum and proximal small intestine. The contrast medium is administered rectally for examination of the distal small intestine and the colon.

The most widely used contrast agent for the visualization of the GI tract is barium sulfate administered as a suspension orally or rectally as an enema. (See, for example, U.S. Pat. Nos.: 2,659,690; 2,680,089; 3,216,900; 3,235,462; 4,038,379 and 4,120,946) Notwithstanding its relatively good contrast characteristics, negligible absorption from the GI tract following oral or rectal administration and speedy excretion from the body, barium sulfate has certain disadvantages. In the presence of intestinal fluids it lacks homogeneity and poorly adheres to mucus membranes which can result in poor X-ray images. In the colon, when administered as an enema, it flocculates and forms irregular clumps with fecal matter.

Iodinated organic compounds have also been used as GI contrast agents since the iodine atom is an effective X-ray absorber. They have the most versatility and are utilized in the widest variety of procedures. They are very absorptive of X-rays with which the iodine interacts and produce a so-called photoelectric effect which is a large magnification in contrast caused by the photons stopped in the iodine-containing medium. The magnification of contrast exceeds the level that would be expected from relative changes in density. Because of this magnification, relatively low concentrations of the contrast agent can be utilized. (For iodinated agents see, for example, U.S. Pat. Nos.: 2,786,055; 3,795,698; 2,820,814; 3,360,436; 574,718; 3,733,397; 4,735,795 and 5,047,228.)

The desiderata for an ideal GI contrast agent includes: good. toxicological profile; the ability to fill the entire bowel/lumen and evenly coat the gut mucosa so that the presence of the bowel is detectable when the lumen is not distended; and nonirritation to the intestinal mucosa; and passage through the GI tract without producing artifacts or stimulating vigorous intestinal peristalsis.

We have found that compounds having these and other desirable characteristics in the GI tract should preferably have the following properties for inclusion in a suitable pharmaceutically acceptable vehicle for oral or rectal administration:

a partition coefficient, i.e. the ratio of hydrophobicity to hydrophilicity of about 10 or higher;

a melting point of less than about 80° C.; and a molecular weight of at least about 200.

We have found that certain compounds hereinafter described possess these desirable properties when used in aqueous oral and rectal formulations for examination of the GI tract utilizing X-rays and CT scans.

SUMMARY OF THE INVENTION

In accordance with the invention, there is provided an x-ray contrast composition comprising solid particles of a contrast agent having:

a partition coefficient of about 10 or higher, and preferably, from about $10^2$ to about $10^8$;

a melting point of less than 80° C., and preferably less than 60° C.; and a molecular weight of at least 200, and preferably from about 200 to about 2,000; and a pharmaceutically acceptable aqueous carrier therefor.

In accordance with the present invention, there is also provided an x-ray contrast composition comprising a liquid x-ray contrast agent having:

a partition coefficient of about 10 or higher, and preferably, from about $10^2$ to about $10^8$;

a molecular weight of at least 200, and preferably from about 200 to about 2,000; and a pharmaceutically acceptable aqueous carrier therefor.

In accordance with the invention there is further provided a method for x-ray diagnostic imaging of the GI tract which comprises orally or rectally administering to the patient an effective contrast producing amount of one of the above-described x-ray contrast compostions.

The composition for radiological examination of the GI tract comprises a compound of the formula or a pharmaceutically acceptable salt thereoff;

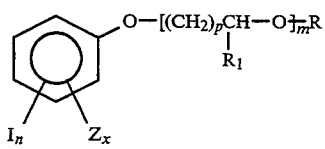

wherein $Z$=H, halo, $C_1$–$C_{20}$ alkyl, cycloalkyl, lower alkoxy, alkoxycarbonyl, cyano, where the alkyl and cycloalkyl groups can be substituted with halogen or halo-lower-alkyl groups;

$R$=$C_1$–$C_{25}$ alkyl, cycloalkyl,

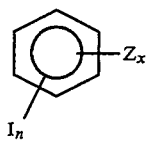

or halo-lower-alkyl; each of which may be optionally substituted with halo, fluoro-lower-alkyl, aryl, lower-alkoxy, hydroxy, carboxy, lower-alkoxy carbonyl or lower-alkoxy-carbonyloxy, ($CR_1$, $R_2$, $R_3$ and $R_4$ are independently H, or lower-alkyl, optionally substituted with halo;

x is 1–4;
n is [1–5]1–4;
m is 1–15;
p is 1–20; and
Q is H, lower-alkyl, lower-alkenyl, lower-alkynyl, lower-alkylene, aryl, or aryl-lower alkyl.

As used herein, the term halogen (or halo) means fluorine, chlorine, bromine or iodine.

As used herein, the term cycloalkyl means carbocyclic rings having from three to eight ring carbon atoms including cyclopropyl, cyclobutyl, cyclopentyl, cyclohexyl and cyclooctyl which may be substituted on any ring carbon atom thereof by one or more lower-alkyl groups, lower-alkoxy groups or halogens.

As used herein the terms lower-alkyl and lower-alkoxy means monovalent aliphatic radicals, including branched chain radicals, of from one to ten carbon atoms. Thus, the lower-alkyl moiety of such groups include, for example, methyl, ethyl, propyl, isopropyl, n-butyl, sec-butyl, t-butyl, n-pentyl, 2-methyl-3-methylpentyl, 1-ethylbutyl, 2-ethylbutyl, 2-hexyl, 3-hexyl, 1,1,3,3-tetramethylpentyl, 1,1-dimethyloctyl and the like.

As used herein, the term lower-alkenyl and lower-alkynyl means monovalent, unsaturated radicals including branched chain radicals of from three to ten carbon atoms and thus include 1-ethenyl, 1-(2-propenyl), 1-(2-butenyl), 1-(1-methyl-2-propenyl), 1-(4-methyl-2-pentenyl), 4,4,6-trimethyl-2-heptenyl, 1-ethynyl, 1-(2-propynyl), 1-(2-butynyl), 1-(1-methyl-2-propynyl), 1-(4-methyl-2-pentynyl) and the like.

As used herein, the term alkylene means divalent saturated radicals, including branched chain radicals of from two to ten carbon atoms having their free valences on different carbon atoms and thus includes 1,2-ethylene, 1,3-propylene, 1,4-butylene, 1-methyl-1,2-ethylene, 1,8-octylene and the like.

As used herein, the term aryl means an aromatic hydrocarbon radical having six to ten carbon atoms. The preferred aryl groups are phenyl, substituted phenyl and naphthyl substituted by from one to three, the same or different members of the group consisting of lower-alkyl, halogen, hydroxy-lower-alkyl, alkoxy-lower-alkyl and hydroxy.

The x-ray contrast compound can comprise one, two, three or more iodine atoms per molecule; preferred species contain at least two, and more preferably, at least three iodine atoms per molecule.

The solid x-ray contrast agents in particulate forms useful in the practice of the present invention can be prepared by techniques known in the art. The solid agents are comminuted to the desired size using conventional milling methods, such as airjet or fragmentation milling. We have found that an effective average particle size of less than about 100μ provides for good distribution and coating in the GI tract. As used herein, particle size refers to a number average particle size as measured by conventional techniques, such as sedimentation field flow fractionation and disk centrifugation. An effective average particle size of less than about 100μ means that at least about 90% of the particles have a weight average particle size of less than about 100μ as measured by art recognized techniques.

A method for diagnostic imaging of the GI tract for use in medical procedures in accordance with this invention comprises orally or rectally administering to the mammalian patient in need of an x-ray examination, an effective contrast producing amount of a composition of the present invention. After administration at least a portion of the GI tract containing the administered composition is exposed to x-rays to produce an x-ray image pattern corresponding to the presence of the contrast agent, then the x-ray image is visualized and interpreted using techniques known in the art.

DETAILED DESCRIPTION OF THE INVENTION

Compounds of the present invention can be made according to the schematic procedure shown or other methods using commercially available starting materials, intermediates and reagents. Starting materials, reagents and solvents can be obtained from chemical suppliers such as Aldrich, Baker and Eastman Chemical Companies, or they may be prepared by techniques known in the art.

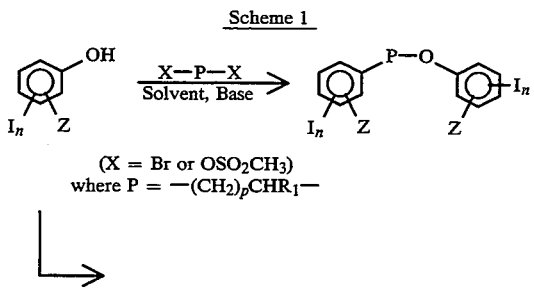

Scheme 1

(X = Br or $OSO_2CH_3$)
where P = —$(CH_2)_p CHR_1$—

The following examples will further illustrate the compounds used in the present invention.

EXAMPLE 1

Bis-(4-iodophenyl) ether of polyethylene-glycol-400

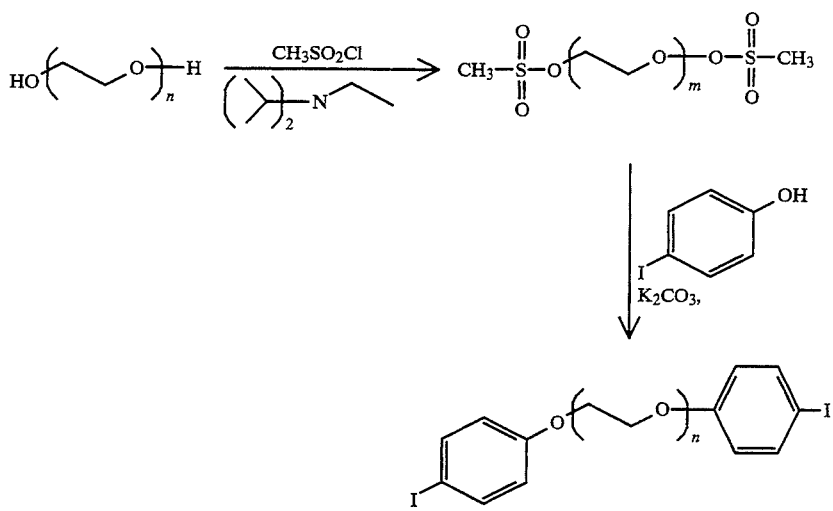

Preparation of bis-mesylate of polyethylene-glycol-400 (PEG-400)

To a solution of PEG-400 (40.0 g, 100 mmol) in dry $CH_2Cl_2$ (200 ml) at 4° C. was added diisopropylethylamine (43.5 ml, 250 mmol). After 10 min, methanesulfonyl chloride (17.0 ml, 220 mmol) was added as a solution in $CH_2Cl_2$ (40 ml) over a period of 0.4 hr. After 2.5 hrs, the reaction was diluted to 500 ml with cold $CH_2Cl_2$ and poured over ice-cold 1 N aqueous HCl (400 ml). The layers were separated. The organic layer was washed with water (300 ml) and brine (300 ml), dried ($Na_2SO_4$), filtered and evaporated in vacuo to provide the bis-mesylate as a light yellow oil (56.0 g, 99%). $^1H$ NMR spectrum was satisfactory.

B. Preparation of Bis-(4-iodophenyl) ether of polyethylene glycol-400

The bis-mesylate of PEG-400 (15.3 g, 27.5 mmol) in dry DMF (110 ml) was reacted with 4-iodophenol (12.1 g, 55.0 mmol) and potassium carbonate (7.6 g, 55.0 mmol) at 77° C. under an atmosphere of $N_2$. After stirring for 16 hrs, the reaction was allowed to cool, diluted with DMF, filtered through a pad of celite and evaporated in vacuo. The resulting residue was taken up with EtOAc (500 ml), washed with 1 M aqueous sodium hydroxide (200 ml), water (200 ml) and brine (200 ml), dried ($Na_2SO_4$), filtered, and evaporated in vacuo to provide a light brown syrup. Flash column chromatography (silica, 1% - 5%; $CH_3OH$ in $CH_2Cl_2$) provided bis-(4-iodophenyl) ether of polyethylene glycol-400 which was slightly contaminated with unreacted mesylates. The product was further purified by dissolving 10.5 g in DMF (100 ml). Sodium methoxide (400 mg) was added. The reaction flask was immersed in an oil bath and warmed to 93° C. After stirring for 16 hrs, the reaction was allowed to cool, diluted with EtOAc (500 ml), washed with water (200 ml) and brine (200 ml) repeatedly (3 times), dried ($Na_2SO_4$), filtered and evaporated in vacuo to provide a light yellow syrup. Flash column chromatography (silica, 5% $CH_3OH$ in $CH_2Cl_2$) provided bis-(4-iodophenyl) ether of polyethylene glycol-400 as a light yellow syrup (8.3 g). $^1H$ NMR (300 MHz) analysis of the product indicates that the average number of ethylene oxide units is eight (n=8). Title Compound: $^1H$ (300 MHz) and $^{13}C$ (75 MHz) NMR spectra were consistent with the desired product.

EXAMPLE 2

1,8-Bis-O-(2,4,6,triiodophenyl)-tripropylene glycol

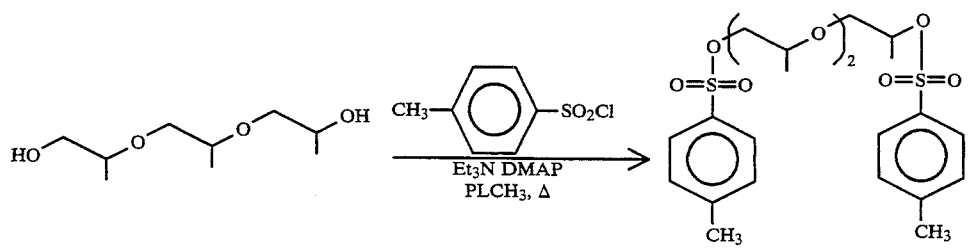

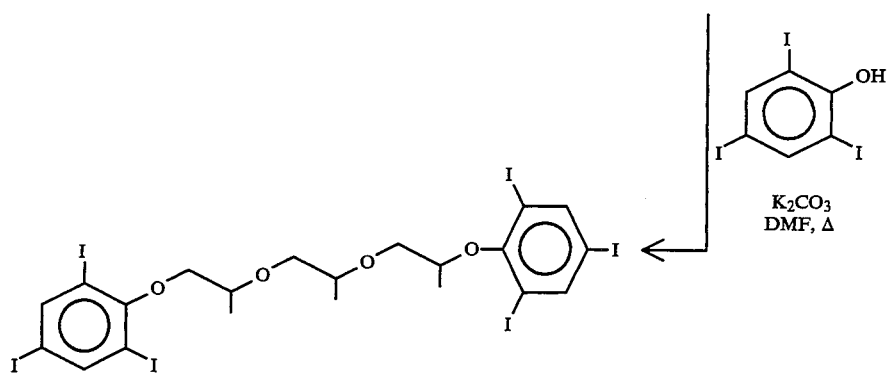

A. Preparation of tripropylene glycol-di-p-tosylate

To a solution of tripropylene glycol (19.3 g, 100 mmol) in anhydrous toluene (400 ml) was added p-toluenesulfonyl chloride (76.5 g, 401 mmol), triethylamine (62.7 ml, 450 mmol) and dimethylamino pyridine (1.22 g, 10 mmol). The reaction was immersed in an oil bath which was warmed to 66° C. over 0.5 hr. After stirring under $N_2$ for 20 hrs, the reaction was allowed to cool, diluted with toluene (500 ml), filtered through a pad of celite and evaporated in vacuo. The resulting residue was dissolved in $CH_2Cl_2$ (1 liter), washed with 5% aqueous sodium bicarbonate (500 ml), water (500 ml) and brine (500 ml), dried ($Na_2SO_4$), filtered and evaporated in vacuo. Flash column chromatography (silica, $CH_2Cl_2$) afforded tripropylene glycol di-p-tosylate (9.6 g, 19.2%) as a viscous yellow oil.

Preparation of 1,8-bis-O-(2,4,6-triiodophenyl)-tripropylene glycol

To a stirred solution of tripropylene glycol di-p-tosylate (9.5 g, 18.9 mmol) in dry DMF (76 ml) was added triiodophenol (18.8 g, 39.8 mmol) and potassium carbonate (5.48 g, 39.7 mmol). The reaction was immersed in an oil bath which was heated to 76° C. The reaction was stirred at 76° C. for 41 hrs. At the end of this period the reaction was diluted with DMF (200 ml), filtered through a pad of celite and evaporated in vacuo. The resulting residue was dissolved in ether (300 ml), washed with 1 M aqueous sodium hydroxide (100 ml), water (2×100 ml) and brine, dried ($Na_2SO_4$), filtered and evaporated in vacuo. Flash column chromatography (silica, 1:1, $CH_2Cl_2$: hexanes) provided 1,8-bis-O-(2,4,6-triiodophenyl)-tripropylene glycol (14.8 g, 13.4 mmol) as a light yellow glass.

Title Compound: $^1H$ (300 MHz) and $^{13}C$ (75 MHz) NMR spectra were consistent with the desired product. Calculated for $C_{21}H_{22}O_4I_6$: C, 22.93; H, 2.02; I, 69.23. Found: C, 23.23, H, 2.00; I, 69.55.

EXAMPLE 3

1,11-bis-(2,4,6-triiodophenoxy)-3,6,9-trioxaundecane

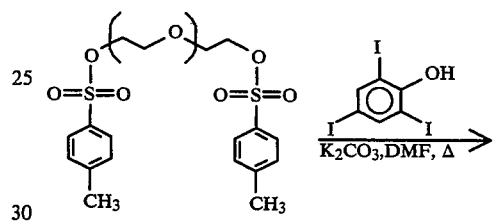

To a solution of tetraethylene glycol di-p-tosylate (15.0 g, 29.8 mmol) in DMF (120 ml) was added triiodophenol (31.0 g, 65.7 mmol) and potassium carbonate (9.0 g, 65.2 mmol). The reaction flask was immersed in an oil bath which was heated to 74° C. over a period of 0.5 hr. The reaction was stirred under an $N_2$ atmosphere for 17 hrs. At the end of this period, TLC analysis indicated the reaction was complete. The reaction was cooled, diluted with DMF and filtered through a pad of celite. The filtrate was evaporated in vacuo to yield a light brown solid which was stirred with ethyl acetate and filtered to yield a light grey solid (21.0 g). A portion of this product (10 g) was recrystallized from hexanes to give 1,11bis-(2,4,6-triiodophenoxy)-3,6,9-trioxaundecane (9.4 g) as a white solid. Mp (from hexanes): 126–128° C.

Title Compound: $^1H$ (300 MHz) and $^{13}C$ (75 MHz) NMR spectra were consistent with the desired product. FAB/MS: MH+: 1103. Calculated for $C_{20}H_{20}O_5I_6$: C, 21.80; H, 1.83; I, 69.11. Found: C, 22.18, H, 1.79; I, 69.41.

EXAMPLE 4

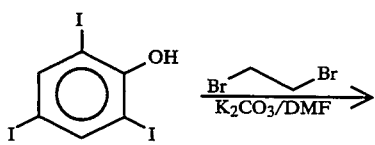

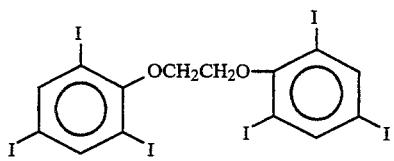

Using the procedure described for the preparation of 1,12-bis-(2,4,6-triiodophenoxy)-dodecane, 1,2-bis-(2,4,6-triiodophenoxy)ethane was prepared in 32% yield from triiodophenol (1.87 g, 3.96 mmol), milled potassium carbonate (0.66 g, 4.78 mmol, 1.2 eq) and dibromoethane (0.18 ml, 1.98 mmol) in DMF (12 ml) at 60° C. for 12 hours. Recrystallization from DMF gave white needles (1.2 g, 32%), Mp. 288°-289° C. after drying under high vacuum/110° C. Title Compound: $^1$H (300 MHz) and $^{13}$C (75 MHz) NMR spectra were consistent with the desired product. Calculated for $C_{14}H_8I_6O_2$: C, 17.34; H, 0.83; I, 78.53; Found: C, 17.60, H, 0.82; I, 78.30.

EXAMPLE 5

Bis-O-(2,4,6-triiodophenyl) ether of polyethylene glycol 400

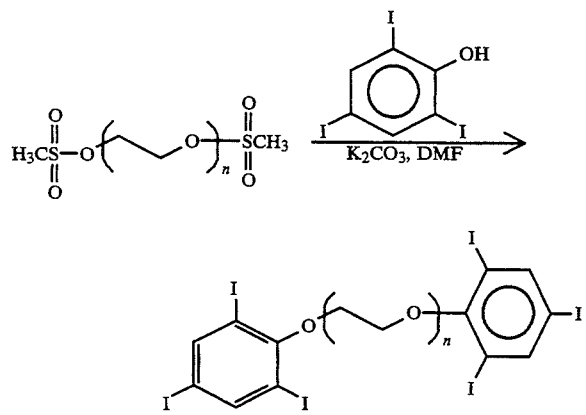

The bis-mesylate of polyethylene glycol-400 (18.7 g, 33.6 mmol) was reacted with triiodophenol (36.5 g, 77.4 mmol) and potassium carbonate (10.7 g, 77.5 mmol) in dry DMF (13.6 ml) as per bis-O-(2,4,6-triiodophenyl) ether of polyethylene glycol 400 except at a temperature of 76° C. for 14 hrs followed by heating at 92° C. for 4 hrs. At the end of this period, the reaction was allowed to cool, diluted with DMF, filtered through celite and evaporated in vacuo. The residue was taken up in EtOAc (600 ml), washed with water (250 ml), 1 N aqueous sodium hydroxide (250 ml), water (2×250 ml) and brine (250 ml), dried (Na2SO4), filtered and evaporated in vacuo to give a dark brown syrup. Flash column chromatography (silica, 1:39-1:19, CH3OH : CH2Cl2) provided a brown syrup. This product was further purified by dissolution in EtOAc (500 ml), washing with saturated aqueous sodium thiosulfate (2×200 ml) and brine (200 ml), drying (Na2SO4) and filtering. The flitrate was treated with decolorizing carbon (10 g), heated to boiling (0.25 h), filtered and evaporated in vacuo to provide bis-O-(2,4,6-triiodophenyl) ether of polyethylene glycol-400 (29 g). $^1$H NMR analysis (300 MHZ) of the product indicates that the average number of the ethylene oxide units is eight (n=8). Title Compound: $^1$H (300 MHz) and $^{13}$C (75 MHz) NMR spectra were consistent with the desired product.

EXAMPLE 6

1-(3-Iodophenoxy)-3,6,9-trioxadecane

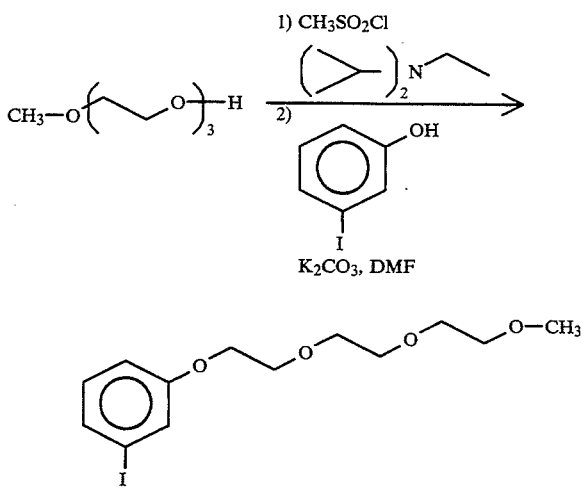

Preparation of the mesylate of triethylene glycol monomethyl ether

The mesylate was prepared via standard protocol from triethylene glycol monomethyl ether (8.2 g, 50.0 mmol), methanesulfonyl chloride (4.6 ml, 59.4 mmol) and diisopropylethylamine (11.3 ml, 64.9 mmol) in dichloromethane (100 ml) in 99% yield.

B. Preparation of 1-(3-Iodophenoxy)-3,6,9-trioxadecane

To a solution of 1-[(methanesulfonyl)-oxy]-3,6,9-trioxadecane (11.6 g, 47.9 mmol) in dry DMF (145 ml) was added 3-iodophenol (10.6 g, 48.2 mmol) and potassium carbonate (6.6 g, 47.8 mmol). The reaction was immersed in an oil bath which was warmed to 68° C. over a period of 0.5 hr. The reaction was stirred at this temperature under an N2 atmosphere for 16 hrs and then at 82° C. for an additional 2 hrs. At the end of this period, the reaction was cooled, diluted with DMF, filtered through a pad of celite and evaporated in vacuo. The resulting residue was taken up into ethyl acetate (500 ml), washed with water (200 ml), 1 N aqueous sodium hydroxide (200 ml) and brine (200 ml), dried (Na2SO4), filtered and evaporated in vacuo to provide a light brown oil. Flash column chromatography (silica, 1:3 to 1:2; EtOAc:hexane) provided 1-(3-iodophenoxy)-3,6,9-trioxadecane as a light yellow oil (10.8 g, 37.1%). Title Compound: $^1$H (300 MHz) and $^{13}$C (75 MHz) NMR spectra were consistent with the desired product. Calculated for $C_{13}H_{10}O_4I$: C, 42.52; H, 5.49; I, 34.56. Found: C, 42.50, H, 5.13; I, 34.78.

EXAMPLE 7

1,3-Bis-(2,4,6-Triiodophenoxy)-butane

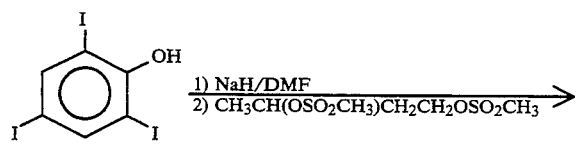

-continued

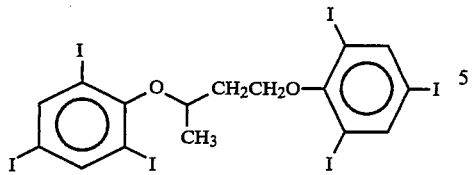

A mixture of triiodophenol (5.78 g, 12.3 mmol) and sodium hydride (0.49 g, 60% dispersion, 12.3 mmol) in DMF (15 ml) was stirred at room temperature for 1 hour and then a solution of 1,3-bis-(methanesulfonyloxy) butane (1.37 g, 5.58 mmol) in DMF (5 ml) was added. The mixture was heated to 90° C. for 6 hours and then poured into water after cooling. Ethyl acetate was added and the mixture was allowed to stand overnight. The precipitated solid was collected and dried to give 3.0 g (54%) of the desired product, Mp 173–175° C.

Title Compound: $^1$H (300 MHz) and $^{13}$C (75 MHz) NMR spectra were consistent with the desired product. Calculated for $C_6H_{12}I_6O_2$: C, 18.26; H, 1.21; I, 76.32; Found: C,19.35, H, 1.16; I, 76.27.

EXAMPLE 8

1-(3-Iodophenoxy)-6-(2,4,6-triiodophenoxy)-hexane

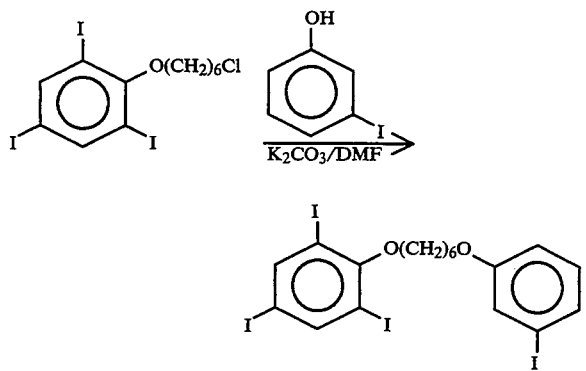

A mixture of potassium carbonate (3.0 g, 21.9 mmol, 1.1 eq), 3-iodophenol (4.4 g, 19.9 mmol) and 6-(2,4,6-triiodophenoxy)-1-chlorohexane (11.75 g, 19.9 mmol) in 50 ml of DMF was heated to 110° C. for 1.5 hours and then cooled. The mixture was poured into water and extracted with ethyl acetate. The organic layer was dried (magnesium sulfate) and evaporated to give a solid which was filtered through basic alumina (hexanes-ethyl acetate). The filtrate was concentrated under vacuum leaving the crude product as a solid. Recrystallization from cyclohexane afforded 8.29 g (54%) of the desired product after drying at room temperature under high vacuum, mp 65–66° C.

Title Compound: $^1$H (300 MHz) and 13C (75 MHz) NMR spectra were consistent with the desired product. Calculated for $C_{18}H_{18}I_4O_2$: C, 27.93; H, 2.34; I, 65.59; Found: C, 27.85, H, 2.16; I, 65.53.

EXAMPLE 9

1,12-Bis-(2,4,6-Triiodophenoxy)-dodecane

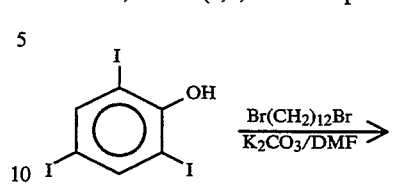

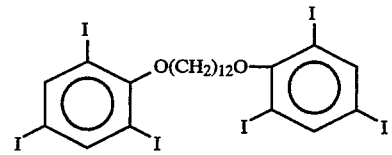

A mixture of triiodophenol (14.4 g, 30.5 mmol), potassium carbonate (4.6 g, 33.6 mmol, 1.1 eq) and 1,12-dibromododecane (5.0 g, 15.2 mmol) in dimethylformamide (30 ml) was heated at 120° C. for 2 hours and then cooled. The reaction mixture was poured into water (400 ml) and ethyl acetate (400 ml) was added. The solid that precipitated was collected, slurried in boiling methanol and then boiling water. The residual solid was recrystallized from dimethylformamide to give the product as a white solid (11.1 g, 66%), mp. 120°–121° C. after drying under high vacuum (0.2 torr) at 90° C.

Title Compound: $^1$H (300 MHz) and $^{13}$C. (75 MHz) NMR spectra were consistent with the desired product. Calculated for $C_{24}H_{28}I_6O_2$: ¼ $((CH_3)_2NCHO)$: C, 26.35; H, 2.66; I, 67.49; Found: C,26.64, H, 2.47; I, 67.38.

Compositions of the Present Invention

The contrast agents may be formulated for administration using physiologically acceptable carriers or excipients in a manner within the skill of the art. The compounds with the addition of pharmaceutically acceptable aids (such as surfactants and emulsifiers) and excipients may be suspended or partially dissolved in an aqueous medium resulting in a dispersion, solution or suspension. However, the oily contrast agents are preferably made into emulsions.

Compositions of the present invention comprise the following pharmaceutically acceptable components based on % w/v:

| | |
|---|---|
| Non-aqueous phase | 1–50 |
| Contrast Agent | 0.001–75 |
| Excipient | 0–20 |
| Aids/Surfactants/Emulsifiers | 0.01–15 |
| Water | q.s. to 100 |

Specific Examples of the compositions of the present invention are shown in Examples 10–12

EXAMPLE NO. 10

| | |
|---|---|
| 1-(3-iodophenoxy)-3,6,9-trioxadecane | 34.6% (w/v) |
| Safflower Oil | 10.0% (w/v) |
| Tween 21 | 5.0% (w/v) |
| Hydroxypropylmethylcellulose (4000 cPs) | 0.5% (w/v) |
| q.s. with water to 100% volume and shake | |

EXAMPLE NO. 11

| | |
|---|---|
| 1-(3-iodophenoxy)-6,-(2,4,6-triiodophenoxy)-hexane | 17.4% (w/v) |
| Dow Corning Medical Antifoam AF | 40.0% (w/v) |
| q.s. with water to 100% volume and shake | |

EXAMPLE NO. 12

| | |
|---|---|
| 1,8-bis-O-(2,4,6-triiodophenyl)-tripropylene glycol | 16.4% (w/v) |
| Simplesse ® Dietary Fat Substitute | 30.0% (w/v) |
| Hydroxypropylmethylcellulose (4000 cPs) | 0.5% (w/v) |
| q.s. with water to 100% volume and shake | |

The nonaqueous phase comprises vegetable oils such as safflower oil; non-metabolizing fat substituents, such as Simplesse; fluorinated hydrocarbons, such as perfluorodecalin; mineral oil and simethicone.

Excipients advantageously used in the formulations include viscosity mediating and stabilizing agents, such as microcrystalline cellulose, ethylcellulose, hydroxypropyl methyl cellulose and gum arabic. Physiologically acceptable substances may also be included, such as sodium citrate, sodium chloride, therapeutic substances, antacid substances and flavoring agents. The inclusion of antimicrobial/antiseptic agents such as methyl para-hydroxybenzoate, ethyl para-hydroxybenzoate, propyl parahydroxybenzoate, benzoic acid or sorbic acid may also be desirable in some formulations.

As known by those skilled in the art, surfactants or emulsifiers can reduce the interfacial tension between two immiscible phases, i.e., oil-inaqueous medium. These agents can be used alone or in combination with other emulsifying agents and surfactants. For example, Dow Corning Medical Antifoam AF, which is a composition of 30% w/v poly (dimethylsiloxane) (simethicone) and silica aerogel, 14% w/v stearate emulsifiers and 0.075% w/v sorbic acid, the balance being water, may be used by itself. Intralipid, which is an emulsion of fatty acids needs the presence of a suspending agent for it to form an acceptable emulsion with contrast agents of the present invention. The amount of such surfactants may be in the range of from 0.01 to 15% w/v of the aqueous formulations, although the amount, in general, is kept as low as possible, preferably in the range of 0.05 to 5% w/v. The surface active agents may be cationic, anionic, nonionic, zwitterionic or a mixture of two or more of these agents.

Suitable cationic surfactants include cetyltrimethyl ammonium bromide. Suitable anionic agents include sodium lauryl sulphate, sodium heptadecyl sulphate, alkyl benzenesulphonic acids and salts thereof, sodium butylnapthalene sulfonate, and sulphosuccinates. Zwitterionic surface active agents are substances that when dissolved in water they behave as diprotic acids and, as they ionize, they behave both as a weak base and a weak acid. Since the two charges on the molecule balance each other out the molecules act as neutral molecules. The pH at which the zwitterion concentration is maximum is known as the isoelectric point. Compounds, such as certain amino acids having an isoelectric point at the desired pH of the formulations of the present invention are useful in practicing the present invention.

In preparing the formulations of the present invention we prefer to use nonionic emulsifiers or surface active agents which, similarly to the nonionic contrast agents, possess a superior toxicological profile to that of anionic, cationic or zwitterionic agents. In the nonionic emulsifying agents the proportions of hydrophilic and hydrophobic groups are about evenly balanced. They differ from anionic and cationic surfactants by the absence of charge on the molecule and, for that reason, are generally less of an irritant than the cationic or anionic surfactants. Nonionic surfactants include carboxylic esters, carboxylic amides, ethoxylated alkylphenols and ethoxylated aliphatic alcohols.

One particular type of carboxylic ester nonionic surface active agents are the partial, for example mono-, esters formed by the reaction of fatty and resin acids, for example of about 8 to about 18 carbon atoms, with polyhydric alcohols, for example glycerol, glycols such as mono-, di-, tetra- and hexaethylene glycol, sorbitan, and the like; and similar compounds formed by the direct addition of varying molar ratios of ethylene oxide to the hydroxy group of fatty acids.

Another type of carboxylic esters is the condensation products of fatty and resin partial acids, for example mono-, esters ethylene oxide, such as fatty or resin acid esters of polyoxyethylene sorbitan and sorbitol, for example polyoxyethylene sorbitan, monotall oil esters. These may contain, for example, from about 3 to about 80 oxyethylene units per molecule and fatty or resin acid groups of from about 8 to about 18 carbon atoms. Examples of naturally occurring fatty acid mixtures which may be used are those from coconut oil and tallow while examples of single fatty acids are dodecanoic acid and oleic acid.

Carboxylic amide nonionic surface active agents are the ammonia, monoethylamine and diethylamine amides of fatty acids having an acyl chain of from about 8 to about 18 carbon atoms.

The ethoxylated alkylphenol nonionic surface active agents include various polyethylene oxide condensates of alkylphenols, especially the condensation products of monoalkylphenols or dialkylphenols wherein the alkyl group contains about 6 to about 12 carbon atoms in either branched chain or particularly straight chain configuration, for example, octyl cresol, octyl phenol or nonyl phenol, with ethylene oxide, said ethylene oxide being present in amounts equal to from about 5 to about 25 moles of ethylene oxide per mole of alkylphenol.

Ethoxylated aliphatic alcohol nonionic surface active agents include the condensation products of aliphatic alcohols having fi om about 8 to 18 carbon atoms in either straight chain or branched chain configuration, for example oleyl or cetyl alcohol, with ethylene oxide, said ethylene oxide being present in equal amounts from about 30 to about 60 moles of ethylene oxide per mole of alcohol.

Preferred nonionic surface active agents include: sorbitan esters (sold under the trade name Span) having the formula:

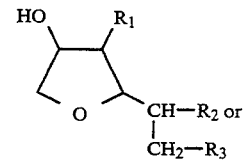

wherein $R_1=R_2=OH$, $R_3=R$ for sorbitan monesters,
$R_1=OH$, $R_2=R_3=R$ for sorbitan diesters,
$R_1=R_2=R_3=R$ for sorbitan triesters, where R=($C_{11}H_{23}$) COO laurate,
($C_{17}H_{33}$) COO for oleate,
($C_{15}H_{31}$) COO for palmitate,
($C_{17}H_{35}$) COO for stearate.

Polyoxyethylene alkyl ethers (i.e. Brijs) having the formula:

$$CH_3(CH_2)_x(O-CH_2-CH_2)_yOH$$

where (x+1) is the number of carbon atoms in the alkyl chain, typically:

| | |
|---|---|
| 12 lauryl | (dodecyl) |
| 14 myristyl | (tetradecyl) |
| 16 cetyl | (hexadecyl) |
| 18 stearyl | (octadecyl) | and y is the number of ethylene oxide groups in the hydrophilic chain, typically 10-60.

Polyethylene sorbitan fatty acid esters, sold under the trade names of Polysorbates 20, 40, 60, 65, 80 & 85.

Polyethylene stearates, such as:
poly(oxy-1,2-ethanediyl)-α-hydro-ω-hydroxyoctadecanoate;
polyethylene glycol monostearate; and
poly(oxy-1,2-ethanediyl)-α-(1-oxooctadecyl )ω-hydroxy-polyethylene glycol monostearate The dosages of the contrast agent used according to the method of the present invention will vary according to the precise nature of the contrast agent used. Preferably, however, the dosage should be kept as low as is consistent with achieving contrast enhanced imaging. By employing as small amount of contrast agent as possible, toxicity potential is minimized. For most contrast agents of the present invention dosages will be in the range of from about 0.1 to about 16.0 g iodine/kg body weight, preferably in the range of from about 0.5 to about 6.0 g iodine/kg of body weight, and most preferably, in the range of from about 1.2 to about 2.0 g iodine/kg body weight for regular X-ray visualization of the GI tract. For CT scanning, the contrast agents of the present invention will be in the range of from about 1 to about 600 mg iodine/kg body weight, preferably in the range of from about to about 200 mg iodine/kg body weight, and most preferably in the range of from about 40 to about 80 mg iodine/kg body weight.

The concentration of the contrast agent should be in the range of from about 0.001% w/v to about 75% w/v of the formulation, preferably from about 0.05% w/v to about 50% w/v and most preferably of from about 0.1% w/v to about 20% w/v.

EXAMPLE NO. 13

An emulsion consisting of 19.1% (w/v) of bis-o-(2,4,6-triiodophenyl) ether of polyethylene glycol-400 and 40.0% (w/v) Dow Corning Medical Antifoam AF in water was administered orally by syringe to three fasted anesthetized rats at a dosage of 10 ml/kg. Flat film x-ray images were taken at timepoints of 15 min., 30 min, 1 hr., 2 hrs., 5 hrs. and 24 hrs. post administration. (25-50 ml/kg of air was added prior to the second x-ray image). Good mucosal coating, uniformity and radiodensity was observed in all portions of the GI tract, superior to barium sulfate suspensions administered under similar conditions.

The invention having been fully described, it will be apparent to one skilled in the art that changes and modifications can be made thereto without departing from the spirit and scope thereof.

What is claimed is:

1. An orally or rectally administerable x-ray contrast composition for visualization of the gastrointestinal tract comprising a contrast agent having the formula, or a pharmaceutically acceptable salt thereof:

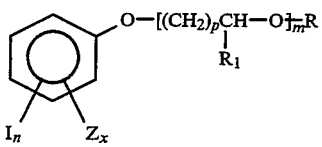

wherein
Z=H, halo, $C_1$-$C_{20}$ alkyl, cycloalkyl, lower alkoxy, alkoxycarbonyl, cyano, where the alkyl and cycloalkyl groups can be substituted with halogen or halo-lower-alkyl groups;
R=$C_1$-$C_{25}$ alkyl, cycloalkyl,

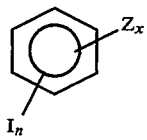

or halo-lower-alkyl; each of which may be optionally substituted with halo, fluoro-lower-alkyl, lower-alkoxy, lower-alkoxy carbonyl or lower-alkoxy-carbonyloxy, $(CR_1R_2)_p$-$(CR_3=CR_4)_mQ$, or $(CR_1R_2)_p$—C≡C-Q;
$R_1$, $R_2$, $R_3$ and $R_4$ are independently H or lower-alkyl, optionally substituted with halo;
x is 1-4;
n is 1-4;
m is 1-15;
p is 1-20; and
Q is H, lower-alkyl, lower-alkenyl, lower-alkynyl, lower-alkylene, aryl, or aryl-lower alkyl, in an aqueous, pharmaceutically acceptable carrier, said pharmaceutically acceptable carrier comprises a surface active agent selected from the group consisting of cetyl trimethylammonium bromide, sodium lauryl sulfate, sodium heptadecyl sulphate, an alkyl benzenesulphonic acid, sodium butylnaphthalene sulfonate, sulphosuccinate, carboxylic esters, carboxylic amides, ethoxylated alkylphenols, ethoxylated aliphatic alcohols, sorbitan esters, polyoxyethylene alkyl ethers and polyoxyethylene sorbitan fatty acid esters.

2. The x-ray contrast composition of claim 1 wherein said contrast agent is selected from the group consisting of: bis-(4iodophenyl) ether of polyethylene glycol-400, 1,8-bis-O-(2,46-triiodophenyl)-tripropylene glycol, 1,11-bis-(2,4,6-triiodophenoxy)-3,6,9-trioxaundecane, 1,2-bis-(2,4,6-triiodophenoxy)-ethane and bis-O-(2,4,6-triiodophenyl) ether of polyethylene glycol-400.

3. The x-ray contrast composition of claim 1 wherein said contrast agent is selected from the group consisting of: 1-(3-iodophenoxy)-3,6,9-trioxadecane, 1,3-bis-(2,4,6-triiodophenoxy)-butane, 1-(3-iodophenoxy)-6-(2,4,6-triiodophenoxy)-hexane and 1,12-bis-(2,4,6-triiodophenoxy)-dodecane.

4. A method of carrying out x-ray examination of the gastrointestinal tract of a patient in need of such examination which comprises orally or rectally administering to the patient an effective contrast producing amount of an x-ray contrast composition comprising: an x-ray contrast agent, or a pharmaceutically acceptable salt thereof, having the formula:

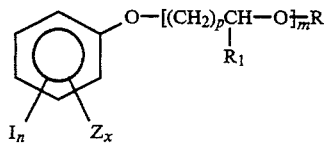

wherein

Z=H, halo, $C_1$-$C_{20}$ alkyl, cycloalkyl, lower alkoxy, alkoxycarbonyl, cyano, where the alkyl and cycloalkyl groups can be substituted with halogen or halo-lower-alkyl groups;

R=$C_1$-$C_{25}$ alkyl, cycloalkyl,

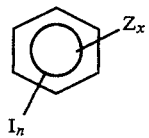

or halo-lower-alkyl; each of which may be optionally substituted with halo, fluoro-lower-alkyl, lower-alkoxy, lower-alkoxy carbonyl or lower-alkoxy-carbonyloxy, $(CR_1R_2)_p$-$(CR_3$=$CR_4)_m$Q, or $(CR_1R_2)_p$—C≡C—Q;

$R_1$, $R_2$, $R_3$ and $R_4$ are independently H or lower-alkyl, optionally substituted with halo;

x is 1-4;
n is 1-4;
m is 1-5;
p is 1-20; and

Q is H, lower-alkyl, lower-alkenyl, lower-alkynyl, lower-alkylene, aryl, or aryl-lower alkyl, in an aqueous, pharmaceutically acceptable carrier, said pharmaceutically acceptable carrier comprises a surface active agent selected from the group consisting of cetyl trimethylammonium bromide, sodium lauryl sulfate, sodium heptadecyl sulphate, an alkyl benzenesulphonic acid, sodium butylnaphthalene sulfonate, sulphosuccinate, carboxylic esters, carboxylic amides, ethoxylated alkylphenols and ethoxylated aliphatic alcohols, sorbitan esters, polyoxyethylene alkyl ethers and polyoxyethylene sorbitan fatty acid esters; and examining said gastrointestinal tract by an x-ray producing apparatus.

5. The method of claim 4 wherein said contrast agent is selected from the group consisting of: bis-(4-iodophenyl) ether of polyethylene glycol-400, 1,8-bis-O-(2,4,6-triiodophenyl)-tripropylene glycol, 1,11-bis-(2,4,6-triiodophenoxy)-3,6,9-trioxaundecane, 1,2-bis-(2,4,6-triiodophenoxy)-ethane and bis-O-(2,4,6-triiodophenyl)-ether of polyethylene glycol-400.

6. The method of claim 4 wherein said contrast agent is selected from the group consisting of: 1-(3-iodophenoxy)-3,6,9-trioxadecane, 1,3-bis-(2,4,6-triiodophenoxy)-butane, 1-(3-iodophenoxy)-6-(2,4,6-triiodophenoxy)-hexane and 1,12-bis-(2,4,6-triiodophenoxy)-dodecane.

* * * * *